United States Patent
Meyerson et al.

(10) Patent No.: US 10,555,671 B2
(45) Date of Patent: Feb. 11, 2020

(54) MOBILE PATIENT CARE SYSTEM

(71) Applicant: Welch Allyn, Inc., Skaneateles Falls, NY (US)

(72) Inventors: Craig M. Meyerson, Syracuse, NY (US); Timothy R. Fitch, Syracuse, NY (US); David J. Maier, Skaneateles, NY (US); Scott Andrew Martin, Warners, NY (US); Tyson B. Whitaker, Arden, NC (US); Kirsten M. Emmons, Batesville, IN (US); Andrew David Clark, Waltham, MA (US); Frederic Bregeon, Saint-Avé (FR); Aalok Mehta, Singapore (SG); Stephen C. Daley, Skaneateles, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 224 days.

(21) Appl. No.: 15/264,954

(22) Filed: Sep. 14, 2016

(65) Prior Publication Data
US 2018/0071157 A1    Mar. 15, 2018

(51) Int. Cl.
| A61B 5/00 | (2006.01) |
| A61B 5/024 | (2006.01) |
| A61B 5/08 | (2006.01) |
| A61B 5/021 | (2006.01) |

(52) U.S. Cl.
CPC .......... *A61B 5/0022* (2013.01); *A61B 5/021* (2013.01); *A61B 5/024* (2013.01); *A61B 5/0816* (2013.01)

(58) Field of Classification Search
CPC ..... A61B 5/0022; A61B 5/01; A61B 5/02055; A61B 5/021; A61B 5/024; A61B 5/0816; A61B 5/742; A61B 5/1059; A61G 7/002; A61G 7/05
USPC .................................................. 600/300, 301
See application file for complete search history.

(56) References Cited

U.S. PATENT DOCUMENTS

| 6,716,167 | B1 | 4/2004 | Henderson et al. |
| 6,832,987 | B2 | 12/2004 | David et al. |
| 7,168,854 | B2 | 1/2007 | Ergun et al. |
| 7,448,680 | B2 | 11/2008 | DiRe |
| 7,702,481 | B2 | 4/2010 | Dionne et al. |
| 8,066,651 | B2 | 11/2011 | Vitton |
| 8,095,204 | B2 | 1/2012 | Smith et al. |
| 8,480,172 | B2 | 7/2013 | Baker et al. |
| 8,926,535 | B2 | 1/2015 | Rawls-Meehan |
| 9,038,216 | B2 | 5/2015 | Buege et al. |

(Continued)

OTHER PUBLICATIONS

Advanced Micro Devices, Dental Assistance Device Adopts 3d Visualization with Amd Embedded G-series Apu S, https://www.amd.com/Documents/54942A-White-Lion-Dental-Case-Study.pdf, 3pgs (2014).

(Continued)

*Primary Examiner* — Nicole F Lavert
(74) *Attorney, Agent, or Firm* — Merchant & Gould P.C.

(57) ABSTRACT

A mobile patient examination system includes a carrier, a patient support, and furnishing. The patient support is height adjustable and connected to the carrier. Also, the patient support includes a display and a physiological sensor. In some instances, the carrier is sized to be transported to different locations within a facility. Alternatively, the carrier is sized to be transported to remote, rural, and/or disaster-related locations.

19 Claims, 6 Drawing Sheets

(56) References Cited

U.S. PATENT DOCUMENTS

| | | |
|---|---|---|
| 9,126,571 B2 | 9/2015 | Lemire et al. |
| 2004/0138924 A1* | 7/2004 | Pristine .................. G06Q 10/04 |
| | | 705/2 |
| 2006/0200029 A1* | 9/2006 | Evans .................... A61B 5/021 |
| | | 600/485 |
| 2007/0035164 A1 | 2/2007 | North |
| 2008/0201847 A1 | 8/2008 | Menkedick et al. |
| 2009/0064415 A1* | 3/2009 | Payne ...................... A47C 7/66 |
| | | 5/620 |
| 2010/0199203 A1 | 8/2010 | Bauer et al. |
| 2010/0212087 A1 | 8/2010 | Leib et al. |
| 2011/0104634 A1 | 5/2011 | Kyöstilä |
| 2011/0202370 A1* | 8/2011 | Green, III ............. G06F 19/328 |
| | | 705/3 |
| 2013/0154296 A1* | 6/2013 | Blackwell .............. A61G 3/001 |
| | | 296/24.38 |
| 2014/0058213 A1* | 2/2014 | Abu-Tarif ............ A61B 5/0205 |
| | | 600/301 |
| 2015/0216755 A1 | 8/2015 | Menke et al. |

OTHER PUBLICATIONS

Benq Medical Technology Corp., TriMax 650NS Series brochure, http://www.xcelsitas.com/index.php/selected2/trimax-650ns-series.html, 6pgs (2015).

ADA National Network, Accessible Medical Examination Tables and Chairs, https://adata.org/sites/adata.org/files/files/BestPracticesExamTablesChairs_6-6.pdf, 5pgs (2014).

\* cited by examiner

MOBILE PATIENT CARE SYSTEM

INTRODUCTION

Patient examination occurs in, for example, medical facilities, managed care facilities, and temporary or emergency care locations. Typical patient examinations include evaluation or determination of various physiological parameters of the patient. Usually these evaluations occur with the patient positioned on an exam table.

SUMMARY

Embodiments of the disclosure are directed to a patient examination system. In one aspect, the patient examination system includes a transportable carrier and a patient support connected to the transportable carrier. The patient support includes an upper surface having a first portion and a second portion, where the second portion is capable of being positioned angled relative to the first portion. The patient support is adjustable in at least one of: height and angle of incline. Also, the patient support includes a physiological sensor and a display in communication with the physiological sensor.

In another aspect, a portable medical examination system includes a mobile carrier including at least one wall, a patient support connected to the mobile carrier, and a furnishing. The patient support includes an upper surface having a first portion and a second portion, where the second portion is capable of being positioned angled relative to the first portion. The patient support is height adjustable and includes a physiological sensor configured to measure a physiological parameter of a patient and a touch-screen display in communication with the physiological sensor.

In another aspect, a patient examination system includes a transportable carrier including at least one wall, furnishing, and a patient support connected to the transportable carrier. The patient support includes an upper surface having a first portion and a second portion, where the second portion is capable of being positioned angled relative to the first portion. The patient support is height adjustable and angle of incline adjustable. Also, the patient support includes a physiological sensor and a display in communication with the physiological sensor. The display is a touch screen display including a system manager module. The system manager module is configured to provide on-screen controls for the patient support and the physiological sensor, provide a check-in sequence to a patient, display a physiological measurement received from the physiological sensor, and transcribe during a patient examination.

The details of one or more embodiments are set forth in the accompanying drawings and the description below. Other features, objects, and advantages of these embodiments will be apparent from the description, drawings, and claims.

DESCRIPTION OF THE DRAWINGS

The following drawing figures, which form a part of this application, are illustrative of described technology and are not meant to limit the scope of the disclosure in any manner.

DETAILED DESCRIPTION

Figure 1:
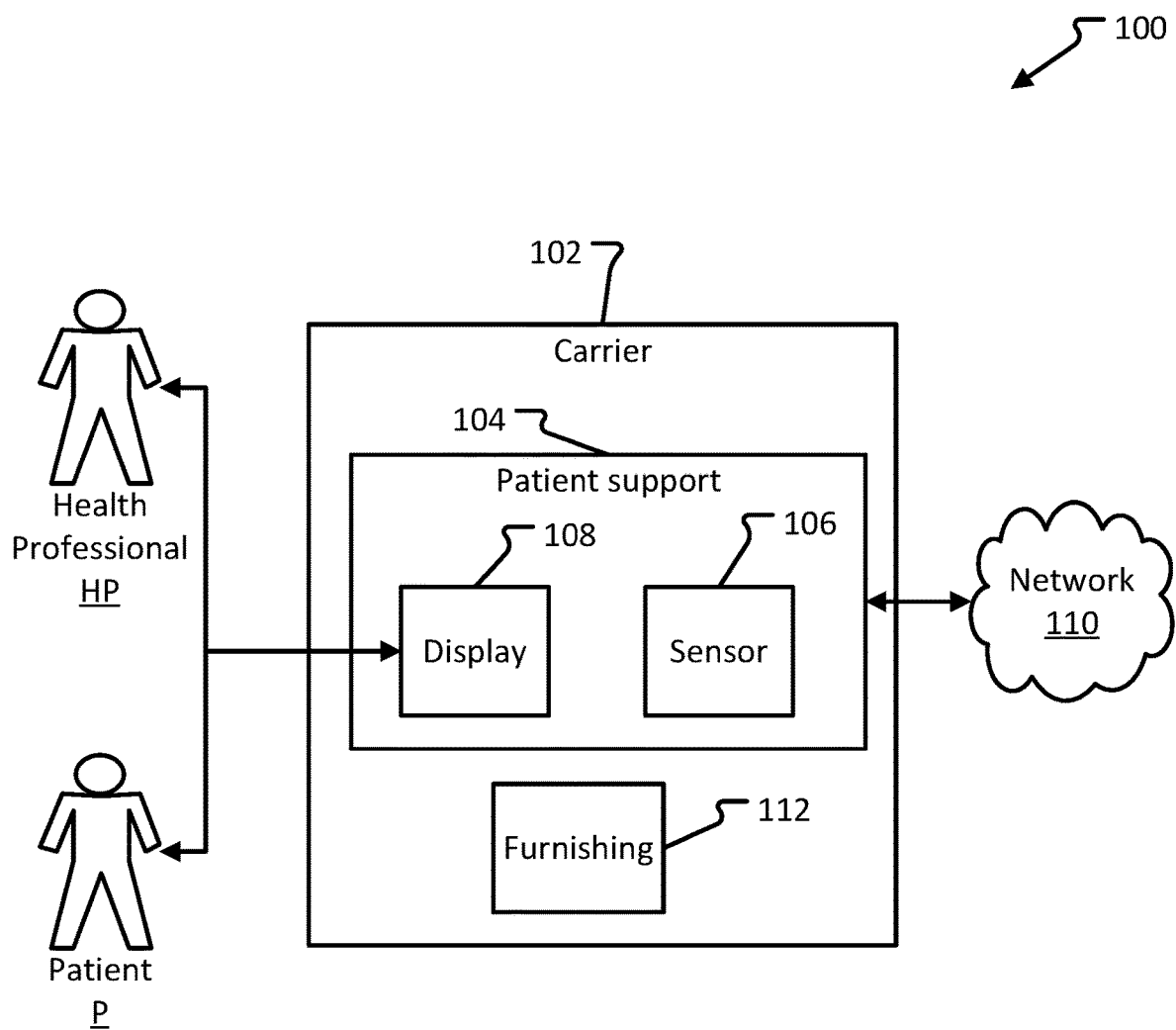
FIG. 1 is a schematic view of an example patient care system.

Various embodiments of the present invention will be described in detail with reference to the drawings, wherein like reference numerals represent like parts and assemblies throughout the several views. Additionally, any examples set forth in this specification are not intended to be limiting and merely set forth some of the many possible embodiments for the claimed invention.

Broadly, the present disclosure is directed to an integrated patient care system. The integrated patient care system improves the patient-doctor experience by centralizing various activities typically performed at disparate locations within an exam room. Generally, the integrated patient care system includes an exam room table having a single user touch point to interface diagnostic equipment and the adjustable exam room table. As discussed below with reference to specific examples, the integrated exam room table improves workflows common to patient examinations.

A typical patient experience may include entering a room and sitting at a first location. In that location, the patient provides personal information to a nurse who is working at a computer workstation. Then the nurse records various vital signs and enters those into the workstation. After the nurse leaves, then a doctor or other health care professional enters the room. With the patient seated at the first location, the doctor sits at the computer workstation, reads data about the patient, and interacts with the patient. Then the patient may be directed to sit at a second location, such as an exam table. There, the doctor performs one or more examinations. After the examinations, the doctor returns to the computer workstation to enter observations, notes, and/or provide any prescriptions or recommended actions. The patient returns to the first location to receive this information. Various aspects of these interactions can be modified per the example systems and methods that are discussed below.

FIG. 1 illustrates a schematic diagram of an example embodiment of a patient care system 100. The example patient care system 100 includes a carrier 102, patient support 104, and furnishing 112. The patient support includes sensor 106 and display 108. A health professional HP interacts with a patient P, and each of the health professional HP and the patient P interact with display 108. The patient care system 100 provides most of the components needed during a typical patient exam. Other embodiments can include more or fewer components.

Carrier 102 provides support for the patient support 104. Generally, the patient care system 100 is portable, meaning that the patient care system 100 can be transported between locations within a facility or between facilities. For example, the patient care system 100 is a portable patient exam system used in a managed care facility, where it typically resides in an exam room but, when necessary, can be moved to the location of a given facility patient. As another example, the patient care system 100 may be transportable to a temporary crisis management area to provide the tools necessary for early treatment and diagnosis.

In various embodiments, carrier 102 is sized differently. For example, carrier 102 is sized to mount to a trailer bed for transportation. Upon reaching the destination, the patient care system 100 is used in a rural or remote area. Additionally, a patient care system 100 so sized may be used in disaster relief-type situations. Still further, carrier 102 may be employed during construction of a health care facility and used as a modular component of the facility. Such a configuration allows the patient care system 100 to be mobile.

As another example, in health care facility or managed care facility, carrier 102 can be transported among various locations and is sized to fit through a door opening. Carrier 102 may include wheels to assist in transporting the carrier 102 between locations within a facility. In some instances, the wheels are detachable.

Patient support 104 is an apparatus that the patient sits on, or lays down on, when interfacing with health professional HP. For example, patient support 104 is an exam table that is height and/or angle adjustable. Alternatively, patient support 104 is an adjustable chair, similar to a dentist's chair. By nature of being adjustable in height and/or angle, the patient support 104 assists in loading and unloading elderly patients and can be adjusted to have an appropriate height for child patients. Example embodiments of patient support 104 are shown in, and described in more detail with reference to, FIGS. 2-5.

Patient support 104 can be in communication with network 110 via a wired or a wireless connection. Optionally, patient support 104 can provide a wireless network accessible by display 108, sensor 106, and/or computing devices used by health professional HP.

The patient support 104 includes sensor 106 capable of obtaining physiological data. Preferably, sensor 106 includes a plurality of sensors, each configured to measure or determine a different physiological parameter of the patient P. For example, sensor 106 is a weight scale, a respiration rate monitor, a blood pressure sensor, a heart rate monitor, and/or a thermometer. Some of these sensors may be integrated into the patient support 104, for example, the weight scale, the respiratory rate monitor, and/or the heart rate monitor. Optionally, sensor 106 is connected to patient support 104, where the sensors may include the sensors listed above in addition to an ophthalmoscope and/or an otoscope.

The patient support 104 additionally includes a display 108 movably secured thereto. Generally, display 108 provides information to and receives input from the patient P and health professional HP. Display 108 is a touch screen display and includes at least some of the components of example computing device 801 shown in FIG. 6. Example modules capable of running on display 108 are shown and described in detail with reference to FIG. 2.

Preferably, display 108 includes a microphone. Display 108 optionally includes a speaker, however, a speaker may be integral to the patient support 104. Usually, display 108 is in communication with an electronic medical record (EMR) and/or electronic health record (EHR) system via network 110. Optionally, display 108 includes a camera capable of capturing still and video images.

Optionally, display 108 is in communication with sensor 106, for example via a wired or wireless connection, and provides controls for the sensor 106. Additionally, display 108 and/or sensor 106 are in communication with network 110.

The network 110 can include any type of wireless network, a wired network, or any communication network known in the art. For example, wireless connections can include cellular network connections and connections made using protocols such as 802.11a, b, and/or g. In other examples, a wireless connection can be accomplished directly between sensor 106 and display 108 using one or more wired or wireless protocols, such as BLUETOOTH, Wi-Fi Direct, radio-frequency identification (RFID), or ZIG-BEE. Other configurations are possible.

Optionally, carrier 102 includes furnishing 112. Furnishing 112 includes items commonly found in patient exam rooms, such as a table, lighting structures, a chair, a hand washing station, etc. Carrier 102 includes one or more of furnishing 112 space permitting and depending upon the intended use of carrier 102. For example, when carrier 102 is used in rural, emergency, and/or modular construction scenarios, carrier 102 generally includes some, most, or all of the items commonly found in patient exam rooms. Alternatively, when carrier 102 is sized to fit through door openings, carrier 102 preferably includes some or none of the items commonly found in patient exam rooms because of space considerations.

Figure 2:
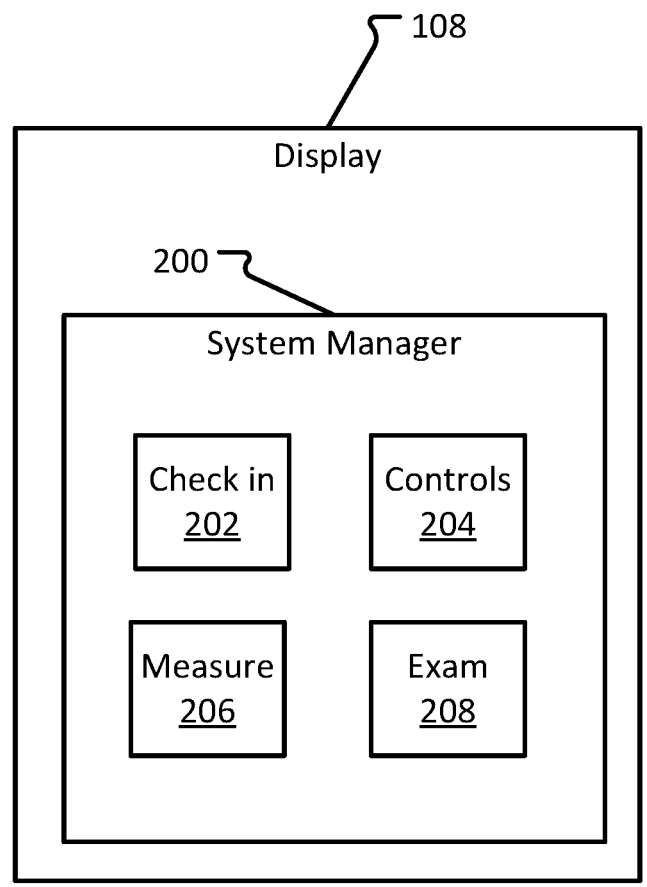
FIG. 2 is a block diagram illustrating components of an example system manager used within the patient care system of FIG. 1.

FIG. 2 is a block diagram illustrating components of an example system manager 200. System manager 200, hosted on display 108, includes check in module 202, controls module 204, measure module 206, and exam module 208. System manager 200 controls some or all of the various components of patient care system 100. Other embodiments can include more or fewer components.

Check in module 202 provides information to, and receives information from, patient P. Generally, check in module 202 runs when a patient P enters an exam room and is seated at the patient support 104. Patient P can interact with display 108 with or without a health professional HP present in the exam room.

While the patient P is waiting for a health professional HP, check in module 202 can prompt the patient P to enter and/or confirm various personal information, such as date of birth, name, preferred pharmacy, emergency contacts, etc. Additionally, check in module 202 can prompt the patient P to provide summaries or data from previous visits. Optionally, check in module 202 can present a patient demographic entry and pre-screening questionnaires, which patient P can complete while waiting for health professional HP.

Controls module 204 provides user-selectable controls for adjusting the one or more components of the patient care system 100. For example, controls module 204 displays one or more controls for adjusting the height and angle of patient support 104. Additionally, control module can display controls for adjusting environmental conditions of the exam room, such as temperature and lighting.

Measure module 206 initiates one or more physiological measurements using sensor 106. Additionally, measure module 206 can display the physiological measurements and/or send the physiological measurements to the patient's EMR/EHR. Measure module 206 can be configured such that, upon receiving physiological data from sensor 106, display 108 presents the physiological data.

Exam module 208 facilitates the health professional's HP examination of the patient P. For example, health professional HP can interact with display 108 to enter data into the patient's P EMR/EHR.

Health professional HP may interact with system manager 200 using voice commands via the exam module 208. As an example, the exam module 208 records notes and/or observations the health professional HP dictates during an examination. Also, system manager 200 can transcribe the health professional's HP instructions for the patient P. Then patient P can access those notes after the exam by, for example, accessing their EMR/EHR and/or having the notes transmitted to them via hyperlink, email, etc. In some instances, results, notes, or other communication made by health professional HP is printed off and provided to the patient P.

In some instances, exam module 208 guides and facilitates the health professional HP in taking pictures. Health professional HP may want to capture images of, for example, a skin condition, mole, bruise, rash, etc., of patient P.

Figure 3:
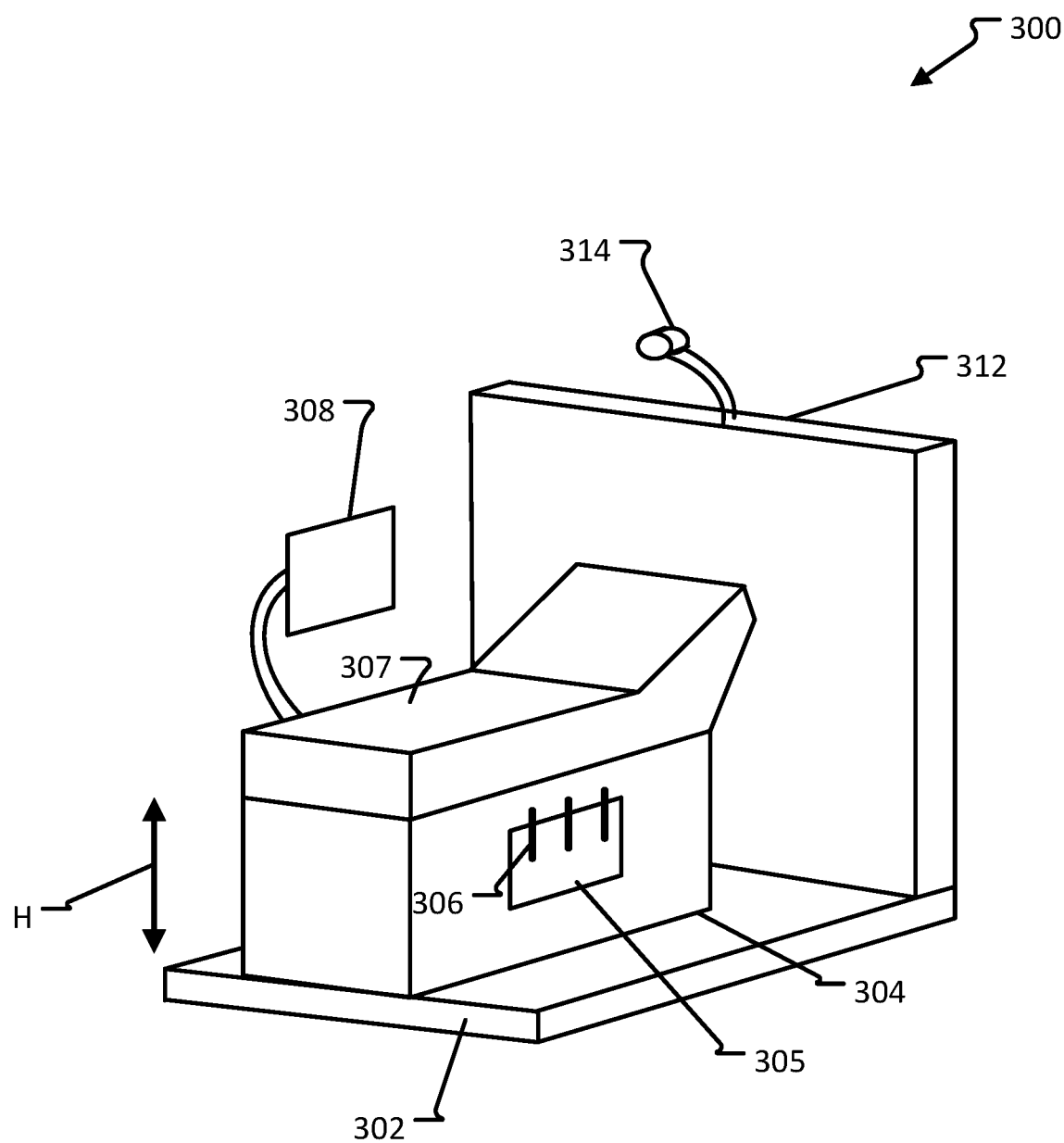
FIG. 3 illustrates an example embodiment of a patient care system.

FIG. 3 illustrates an example embodiment of a patient care system 300. The example patient care system 300 includes carrier 302, patient support 304, sensor mount 305, display 308, and furnishing 312 including light 314. Generally, patient care system 300 is suitable for transportation between locations within a particular facility. Other embodiments can include more or fewer components.

Carrier 302 provides support for patient support 304 and furnishing 312. Carrier 302 is shown without mobility components, such as wheels.

Patient support 304 includes a patient exam table 307. Patient exam table 307 is sized similarly to commercially available exam tables. Preferably, patient exam table 307 is adjustable to be in a "lie flat" position or at a variation of angled positions. As shown in FIG. 3, patient exam table 307 is in an angled position. Patient exam table 307 can include other components, such as movable railings, women's health components, etc., that are not shown in FIG. 3.

Patient support 304 includes components for adjusting the height H of the patient exam table 307. Optionally, the height H of the patient exam table 307 is adjustable via controls provided on display 308.

Patient support 304 also includes sensor mount 305 that supports sensor 306. Preferably, sensor 306 includes more than one type of physiological sensor, such as those discussed above with reference to FIG. 1. Thus, sensor mount 305 typically includes multiple connections and multiple storage areas for the various sensors 306.

Sensor 306 is in communication with display 308 such that display 308 can provide physiological data in real-time. Optionally, sensor 306 is a built-in weight scale.

Display 308 has some or all of the functionality and characteristics of display 108 discussed above with reference to FIGS. 1-2. Preferably, display 308 is connected to patient support 304 such that display 308 is adjustable in horizontal and lateral directions.

Furnishings 312 include a wall and a light 314. Preferably, display 308 provides controls for light 314 and other components of furnishings 312. Examples of other furnishings 312 include mounts for various controls and instruments, such as chargeable hanging ports for various medical instruments like otoscopes, etc. Other example furnishings 312 includes aesthetics like further lighting and/or artistic items (e.g., photographs, paintings, etc.).

Figure 4:
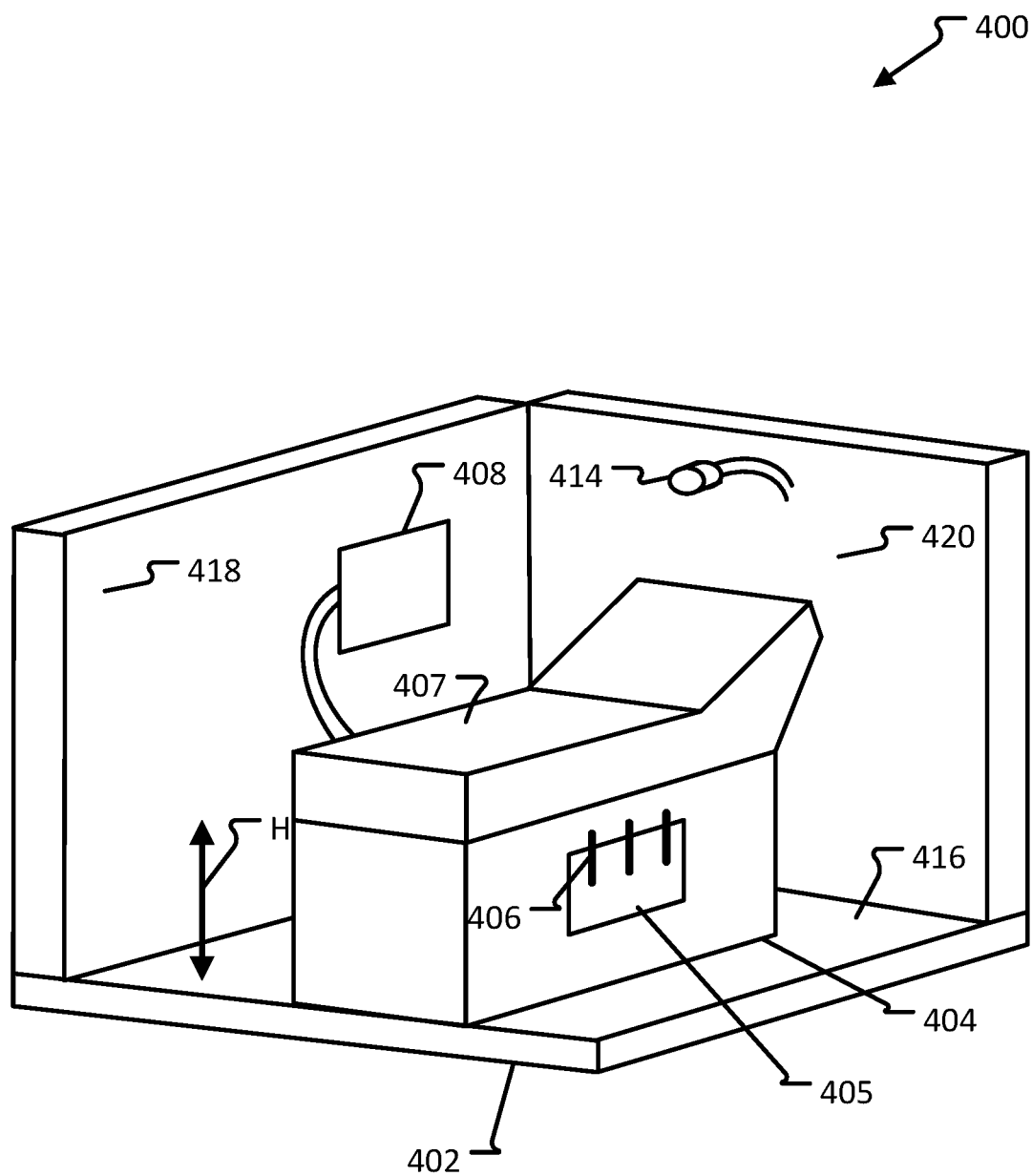
FIG. 4 illustrates an example embodiment of a patient care system.

FIG. 4 illustrates an example embodiment of a patient care system 400. The example patient care system 400 includes carrier 402, patient support 404 with exam table 407, sensor mount 405 and sensor 406, and display 408. Generally, patient care system 400 is suitable for modular installation in a care facility and/or transportation to remote and/or disaster areas. Additionally, patient care system 400 includes most components required for a functional patient exam room. Other embodiments can include more or fewer components.

Carrier 402 includes floor 416 and walls 418 and 420. Generally, carrier 402 is sized to be transported in or on a semi-truck trailer. Preferably, carrier 402 includes another wall opposite wall 418 and/or another wall opposite wall 420. Optionally, carrier 402 includes a wall (ceiling) opposite floor 416.

Figure 5:
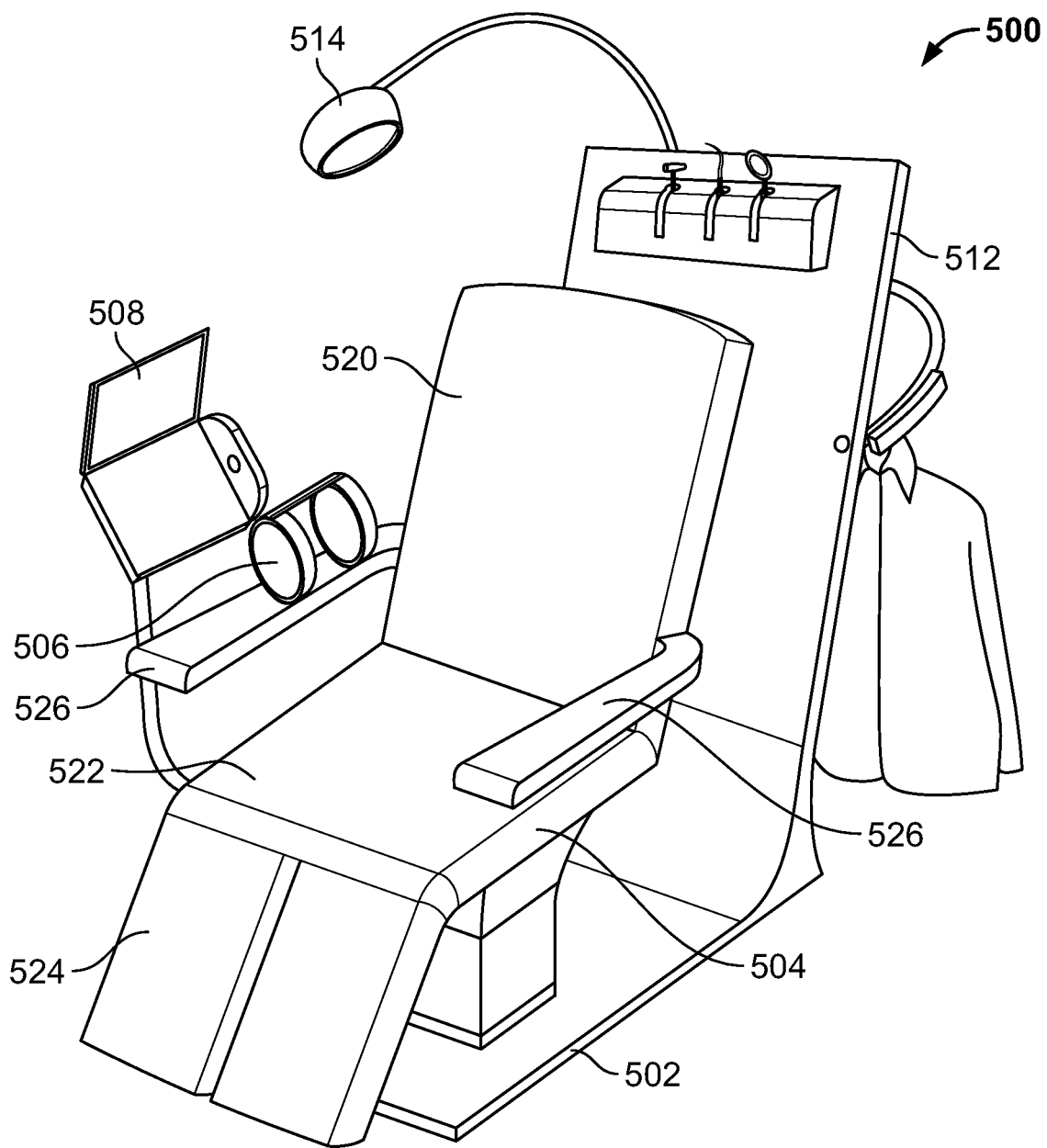
FIG. 5 illustrates an example embodiment of a patient care system.

FIG. 5 illustrates an example embodiment of a patient care system 500. The example patient care system 500 includes carrier 502, patient support 504, sensor 506, display 508, and furnishings 512 including light 514. Generally, patient support 504 can be substituted for patient support 304 and/or 404, described above with reference to FIGS. 3 and 4, respectively. Other embodiments can include more or fewer components.

Patient support 504 is capable of transitioning between an upright position, a substantially lie-flat position, and positions therebetween. Patient support 504 is also height-adjustable.

Patient support 504 includes three sections 520, 522, and 524. Preferably, each section 520, 522 and 524 is rigidly connected to the adjacent sections such that their relative orientations do not change when the angle or height of patient support 504 is adjusted. Optionally, the angle of section 520 and/or 524 is independently adjustable.

Optionally, patient support 504 includes a blood pressure sensor 506. As shown, blood pressure sensor 506 is integrated with arm 526. In some embodiments, display 508 provides instructions guiding the patient through a blood pressure self-test to be performed without a health professional.

Figure 6:
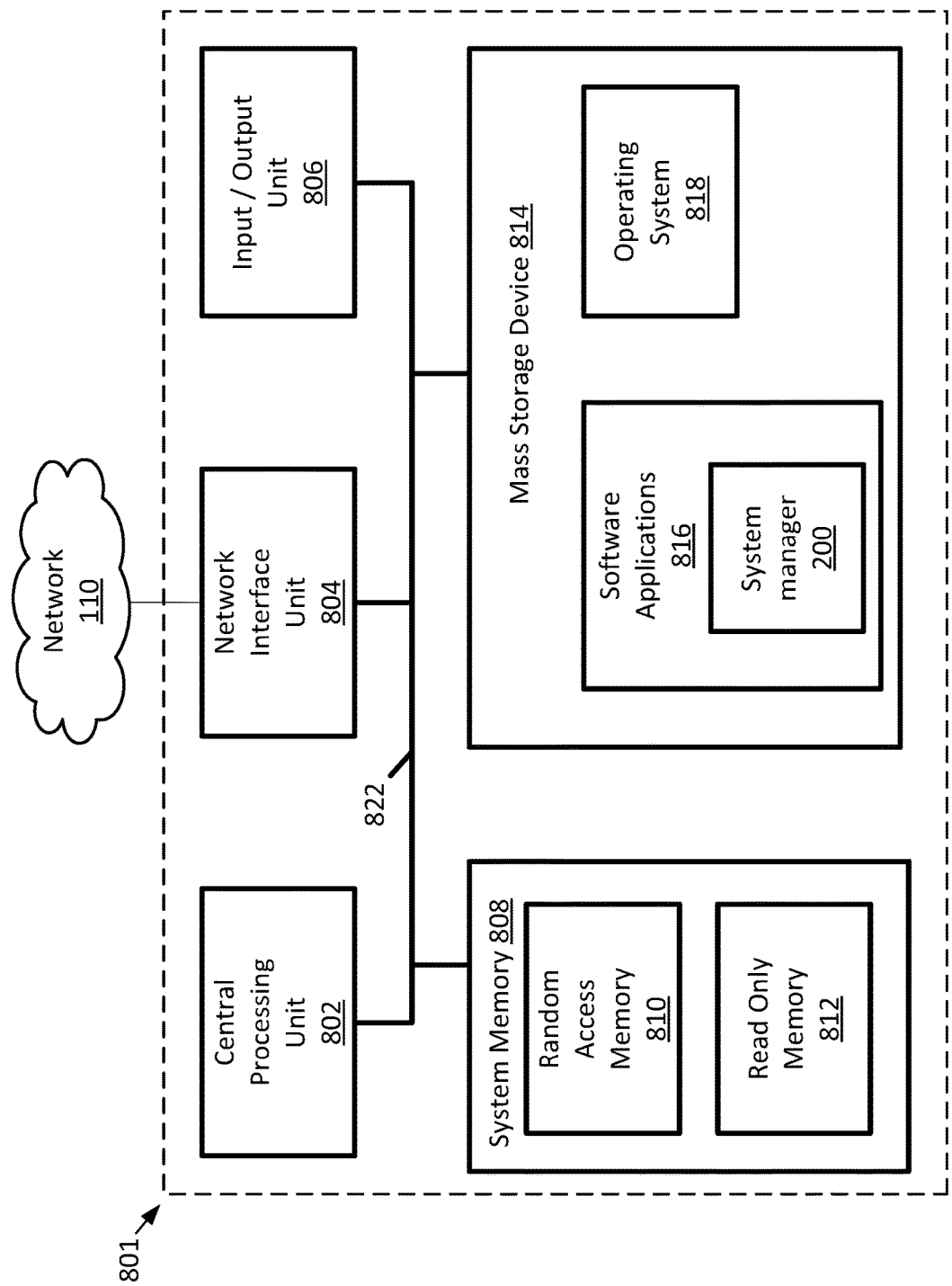
FIG. 6 shows example physical components of a computing device hosting the client system manager module of the display shown in FIG. 1.

FIG. 6 shows an example computing device 801 hosting the system manager 200. As illustrated, the example computing device 801 includes at least one central processing unit ("CPU") 802, a system memory 808, and a system bus 822 that couples the system memory 808 to the CPU 802. The system memory 808 includes a random access memory ("RAM") 810 and a read-only memory ("ROM") 812. A basic input/output system that contains the basic routines that help to transfer information between elements within the example computing device 801, such as during startup, is stored in the ROM 812. The example computing device 801 further includes a mass storage device 814. The mass storage device 814 is able to store software applications 816 and data.

The mass storage device 814 is connected to the CPU 802 through a mass storage controller (not shown) connected to the system bus 822. The mass storage device 814 and its associated computer-readable data storage media provide non-volatile, non-transitory storage for the example computing device 801. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing device 801.

According to various embodiments of the invention, the example computing device 801 may operate in a networked environment using logical connections to remote network devices through the network 110, such as a wireless network, the Internet, or another type of network. The example computing device 801 may connect to the network 110 through a network interface unit 804 connected to the system bus 822. The network 110 may be a protected network, as discussed above. It should be appreciated that the network interface unit 804 may also be utilized to connect to other types of networks and remote computing systems. The example computing device 801 also includes an input/output controller 806 for receiving and processing input from a number of other devices, including a touch user interface display screen, or another type of input device. Similarly, the input/output controller 806 may provide output to a touch user interface display screen or other type of output device.

As mentioned briefly above, the mass storage device 814 and the RAM 810 of the example computing device 801 can store software instructions and data. The software instructions include an operating system 818 suitable for controlling the operation of the example computing device 801. The mass storage device 814 and/or the RAM 810 also store software applications 816, that when executed by the CPU 802, cause the example computing device 801 to provide the functionality of the example computing device 801 discussed in this document. For example, the mass storage device 814 and/or the RAM 810 can store software instructions that, when executed by the CPU 802, cause the example computing device 801 to display received data on the display screen of the example computing device 801.

Although various embodiments are described herein, those of ordinary skill in the art will understand that many modifications may be made thereto within the scope of the present disclosure. Accordingly, it is not intended that the scope of the disclosure in any way be limited by the examples provided.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The invention claimed is:

1. A patient examination system, comprising:
   a transportable carrier configured to fit through a door opening of a patient examination room and to be transported among locations in a patient care facility; and
   a patient support connected to the transportable carrier,
   wherein the patient support includes an upper surface having a first portion and a second portion, the second portion capable of being positioned angled relative to the first portion;
   wherein the patient support is adjustable in at least one of: height and angle of incline; and
   wherein the patient support includes:
     a physiological sensor including at least one of: a blood pressure module, a temperature sensor, an otoscope, and an ophthalmoscope;
     at least one sensor mount integrated within the patient support and configured to support the physiological sensor; and
     a display in communication with the physiological sensor and movably secured to the patient support, the display hosting a system manager configured to:
       provide a check-in sequence to a patient;
       receive interactions from the patient;
       display physiological measurements to a health professional;
       receive voice commands from the health professional;
       record dictation of notes from the health professional; and
       transcribe the notes.

2. The patient examination system of claim 1, wherein the transportable carrier includes detachable wheels.

3. The patient examination system of claim 1, wherein the transportable carrier includes a floor and at least two walls.

4. The patient examination system of claim 3, wherein the transportable carrier includes at least three walls and a ceiling.

5. The patient examination system of claim 1, further comprising furnishings, the furnishings including a light.

6. The patient examination system of claim 1, wherein the display is a touch screen display.

7. The patient examination system of claim 6, wherein the system manager module is configured to provide on-screen controls for the patient support and the physiological sensor.

8. The patient examination system of claim 1, wherein the system manager is in communication with an electronic health record of a patient and the notes are recorded in the electronic health record.

9. The patient examination system of claim 1, further comprising a hand washing station.

10. The patient examination system of claim 1, wherein the system manager is in communication with a camera and is configured to guide a healthcare professional in capturing images during an examination.

11. A portable medical examination system, comprising:
    a mobile carrier including at least one wall and being configured to be transported among patient examination rooms in a patient care facility;
    a patient support connected to the mobile carrier; and
    a furnishing,
    wherein the patient support includes an upper surface having a first portion and a second portion, the second portion capable of being positioned angled relative to the first portion;

wherein the patient support is height adjustable; and
wherein the patient support includes:
- a physiological sensor configured to measure a physiological parameter of a patient including at least one of: blood pressure; and temperature;
- at least one sensor mount configured to support the physiological sensor;
- a touch-screen display in communication with the physiological sensor, the touch-screen display including a camera capable of capturing still and video images; and
- a hand washing station.

12. The portable medical examination system of claim 11, wherein an angle of incline of the patient support is adjustable;
wherein the furnishing includes a light;
wherein the touch-screen display includes a system manager module; and
wherein the system manager module is configured to provide on-screen controls for the patient support and the physiological sensor.

13. The portable medical examination system of claim 12, wherein the system manager module is configured to:
provide a check-in sequence to the patient;
display a physiological measurement received from the physiological sensor; and
transcribe during a patient examination.

14. The portable medical examination system of claim 13, wherein the system manager module is in communication with an electronic health record of the patient.

15. The portable medical examination system of claim 14, wherein the mobile carrier is sized to fit through door openings of patient examination rooms in a patient care facility.

16. The portable medical examination system of claim 14, wherein the mobile carrier is configured to be transported on a trailer.

17. A patient examination system, comprising:
a transportable carrier including at least one wall;
a furnishing; and
a patient support connected to the transportable carrier,
wherein the patient support includes an upper surface having a first portion and a second portion, the second portion capable of being positioned angled relative to the first portion;
wherein the patient support is height adjustable and angle of incline adjustable; and
wherein the patient support includes:
- a first physiological sensor for measuring blood pressure;
- a second physiological sensor for measuring temperature;
- a mount configured to hold the first physiological sensor and the second physiological sensor; and
- a display in communication with the physiological sensor and movably secured to the patient support;
  wherein the display is a touch screen display including a system manager module;
  wherein the system manager module is configured to:
  provide on-screen controls for the patient support and the physiological sensor;
  provide a check-in sequence to a patient;
  display a physiological measurement received from the physiological sensor; and
  transcribe dictated notes from a healthcare professional during a patient examination.

18. The patient examination system of claim 17, wherein the system manager module is in communication with an electronic health record of the patient; and
wherein the transportable carrier is sized to fit through a door opening of a patient examination room.

19. The portable medical examination system of claim 17, further comprising a hand washing station.

* * * * *